United States Patent
Charrat et al.

(10) Patent No.: US 10,393,892 B2
(45) Date of Patent: Aug. 27, 2019

(54) X-RAY DETECTION CIRCUIT FOR A DENTAL RADIOLOGY SENSOR

(71) Applicant: Teledyne e2v Semiconductors SAS, Saint Egrève (FR)

(72) Inventors: Christine Charrat, Saint-Egrève (FR); Caroline Papaix, Quaix-en-Chartreuse (FR); Stéphane Gesset, St.-Laurent-du-Pont (FR)

(73) Assignee: TELEDYNE E2V SEMICONDUCTORS SAS, Saint Egreve (FR)

( * ) Notice: Subject to any disclaimer, the term of this patent is extended or adjusted under 35 U.S.C. 154(b) by 0 days.

(21) Appl. No.: 16/069,227

(22) PCT Filed: Jan. 10, 2017

(86) PCT No.: PCT/EP2017/050411
§ 371 (c)(1),
(2) Date: Jul. 11, 2018

(87) PCT Pub. No.: WO2017/121728
PCT Pub. Date: Jul. 20, 2017

(65) Prior Publication Data
US 2019/0025444 A1    Jan. 24, 2019

(30) Foreign Application Priority Data
Jan. 12, 2016 (FR) .................................... 16 50211

(51) Int. Cl.
*G01T 1/24* (2006.01)
*H04N 5/32* (2006.01)
(Continued)

(52) U.S. Cl.
CPC ............... *G01T 1/247* (2013.01); *A61B 6/14* (2013.01); *A61B 6/4233* (2013.01); *H04N 5/32* (2013.01)

(58) Field of Classification Search
CPC .......... G01T 1/247; A61B 6/14; A61B 6/4233
See application file for complete search history.

(56) References Cited

U.S. PATENT DOCUMENTS

| 5,887,049 A | 3/1999 | Fossum |
| 6,307,915 B1 | 10/2001 | Fröjdh |

(Continued)

FOREIGN PATENT DOCUMENTS

| EP | 2131575 A2 | 12/2009 |
| JP | S61292478 A | 12/1986 |

OTHER PUBLICATIONS

International Search Report and Written Opinion for PCT/EP2017/050411, dated Mar. 24, 2017.

*Primary Examiner* — Hugh Maupin
(74) *Attorney, Agent, or Firm* — Pilloff & Passino LLP; Sean A. Passino; Rachel K. Pilloff

(57) ABSTRACT

A circuit (300) for detecting the appearance of x-rays with a view to triggering a radiological image capture, comprising a set (301) of photodiodes that is connected to a ground ($G_D$), an amplifying circuit (302) and a capacitor (C2), the amplifying circuit (302) comprising an amplifier (AMP) and a voltage source (GEN) and being connected, via a first input, to the output of the set (301) of photodiodes, the capacitor (C2) being connected between the ground ($G_D$) and a second input of the amplifier (AMP), the detecting circuit (300) being characterized in that the amplifying circuit (302) is configured to carry out in succession the steps of:

Charging the capacitor (C2) with a reference voltage ($V_{ref}$) generated by the voltage source (GEN);

(Continued)

Isolating the second input of the amplifier (AMP) from the voltage source (GEN); and
Integrating the current generated by the set (301) of photodiodes.

19 Claims, 4 Drawing Sheets

(51) Int. Cl.
*A61B 6/14* (2006.01)
*A61B 6/00* (2006.01)

(56) References Cited

U.S. PATENT DOCUMENTS

| | | |
|---|---|---|
| 7,592,577 B1 | 9/2009 | Liu |
| 8,119,990 B2 | 2/2012 | Zeller |
| 8,324,587 B2 | 12/2012 | Zeller |
| 2015/0110248 A1* | 4/2015 | Rabi .................. G01T 1/2018 378/62 |
| 2015/0219772 A1* | 8/2015 | Sonoda ............... G01T 1/2018 250/362 |
| 2015/0326805 A1* | 11/2015 | Scott .................. H04N 5/378 348/243 |

* cited by examiner

X-RAY DETECTION CIRCUIT FOR A DENTAL RADIOLOGY SENSOR

FIELD

The invention relates to the field of medical imaging, more precisely for dental applications. In this field, dental radiology sensors exist that in particular consist of image-sensor chips in CMOS technology. A radiological sensor allows an image to be acquired by virtue of the emission of x-rays by a source. The sensor receives these x-rays and converts them into visible rays with a layer of specific material, which layer is referred to as a scintillator and is adhesively bonded to the image sensor. The image is obtained via analog read-out of the generated photons in the photodiodes of the pixels, which are located under the scintillator. Depending on the type of photodiode used, the x-rays may be converted directly into an electrical signal without passing via a scintillator.

DESCRIPTION OF THE PRIOR ART

In order to synchronize the emission of the x-rays and the start of the acquisition of the image, a radiological sensor must necessarily incorporate a system for detecting x-rays. Such a system serves to detect the start of the emission of the x-rays, but also serves to detect the end of the acquisition of the image.

The invention more particularly relates to a circuit for detecting x-rays, which circuit is integrated into a dental radiological sensor.

A circuit for detecting x-rays works on the whole in the following way. It mainly includes a set of photodiodes and an electronic detecting circuit. A flash of x-rays is emitted by a source in the direction of the photodiodes, which convert the x-rays into current. The detecting circuit mainly comprises a transimpedance amplifier, a comparator and an analog output stage. The current produced by the set of photodiodes is delivered to the amplifier, which produces an amplified signal that is then compared, via the comparator, to a threshold in order to perform the detection.

The recommendations of medical standard-setting organizations require constraints be placed on the system. Specifically, the dose of radiation received by patients must be limited to the strict minimum. To do this, two solutions are possible, either the intensity of the flux of emitted x-rays is decreased, or the length of the exposure of the patient, in other words, detection time, is decreased. In both cases, the amplitude of the signal to be detected is decreased and therefore the detection threshold is decreased.

However, the decrease in this threshold leads to another problem. In dental surgeries, a radiological sensor is most often directly connected to the personal computer of the dentist, for example via a USB cable. The reference voltage delivered to the transimpedance amplifier is generated from supply voltages originating from the computer of the dentist, and therefore by a source external to the sensor. These supply voltages are subject to random variations and are also influenced by the electromagnetic environment. The absence of stable reference voltage on an input of the amplifier induces variations in the output signal, which may be such that the detection threshold may be exceeded in an untimely way even in the absence of x-rays.

There is therefore a problem to be solved with a view to designing a circuit for detecting x-rays that is immune to the noise present in the supply voltage, that is effective and reliable in detection terms and that allows a rapid detection with a decreased detection threshold.

SUMMARY

Various circuits for detecting x-rays for dental radiological sensors are known, these circuits in particular being described in U.S. Pat. Nos. 8,119,990, 8,324,587, 6,307,915, 5,887,049 and 7,592,577. The various solutions described in these documents do not allow a reliable and rapid detection of x-rays to be obtained with circuits using an external supply.

The invention provides a differential circuit for detecting x-rays that allows variations in external supply voltages to be made irrelevant and, thus, allows the detection threshold to be decreased without increasing the probability of false alarm related to untimely triggering of the detector because of the influence of noise in the amplified signal.

Thus, one subject of the invention is a circuit for detecting the appearance of x-rays with a view to triggering a radiological image capture, comprising a set of photodiodes that is connected to a ground, an amplifying circuit and a capacitor, the amplifying circuit comprising an amplifier and a voltage source and being connected, via a first input, to the output of the set of photodiodes, the capacitor being connected between the ground and a second input of the amplifier, the detecting circuit being characterized in that the amplifying circuit comprises:
  Means for charging the capacitor with a reference voltage generated by the voltage source during a first portion of an initializing phase of the detecting circuit;
  Means for isolating the second input of the amplifier (AMP) from the voltage source during a second portion of the initializing phase; and
  A capacitor connected between the first input of the amplifying circuit and the output of the amplifier in order to integrate the current generated by the set of photodiodes during a detecting phase following the second portion of the initializing phase.

According to one particular aspect of the invention, the amplifying circuit comprises a first switch connected between the first input and the output of the amplifier.

According to one particular aspect of the invention, the amplifying circuit comprises a second switch connected between the second input of the amplifier and the output of the voltage source.

According to one particular aspect of the invention, the second switch is configured to be in closed position during the first portion of the initializing phase in order to charge the capacitor with a reference voltage generated by the voltage source.

According to one particular aspect of the invention, the second switch is configured to pass to open position during the second portion of the initializing phase in order to isolate the second input of the amplifier from the voltage source.

According to one particular aspect of the invention, the first switch is configured to be in closed position during the initializing phase.

According to one particular aspect of the invention, means are provided for opening the first switch after the end of the initializing phase.

According to one particular aspect of the invention, the capacitor is produced by masking some of the detecting photodiodes and by connecting the output of the masked photodiodes to the second input of the amplifier.

According to one particular aspect of the invention, the masked photodiodes are uniformly distributed within the set of detecting photodiodes.

According to one particular aspect of the invention, the proportion of masked photodiodes with respect to the detecting photodiodes is at least ½.

In one particular variant, the circuit according to the invention furthermore comprises a comparator for comparing the output voltage of the amplifier to a threshold voltage.

According to one particular aspect of the invention, the detecting circuit is able to produce a signal for triggering image capture when the output voltage of the amplifier exceeds the threshold voltage.

Another subject of the invention is a radiological image sensor comprising a circuit for detecting x-rays according to the invention.

BRIEF DESCRIPTION OF THE DRAWINGS

Other features and advantages of the present invention will become more clearly apparent on reading the following description with reference to the appended drawings, which show.

DETAILED DESCRIPTION

Figure 1A:
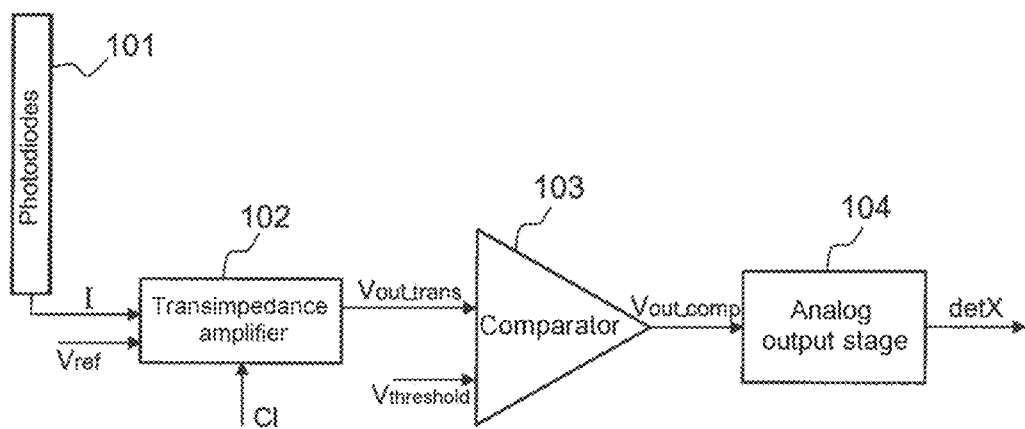
FIG. 1a, a general schematic diagram of a circuit for detecting x-rays.
Figure 1B:
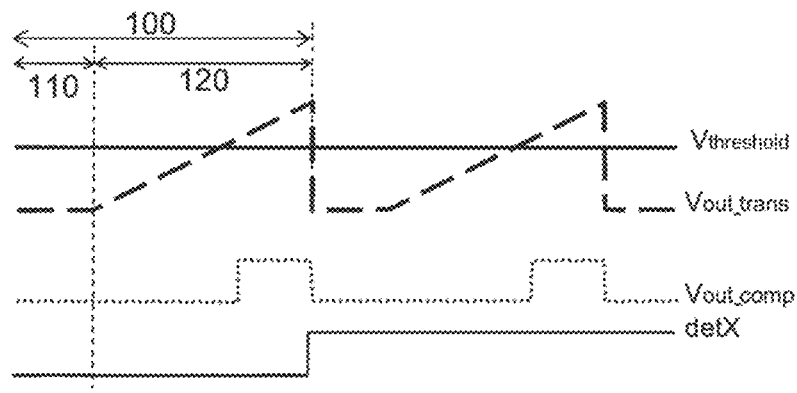
FIG. 1b, a plurality of timing diagrams illustrating the operation of the detecting circuit.

FIG. 1a shows a functional schematic of a circuit for detecting x-rays for a dental radiological sensor. FIG. 1b illustrates, via a plurality of timing diagrams, the general operation of the circuit.

A circuit for detecting x-rays mainly comprises a set 101 of photodiodes that are able to receive a flux of x-rays and to convert it into a current I that is delivered to a first input of a transimpedance amplifier 102. Depending on the type of photodiodes 101 used, the current I is directly or indirectly generated by the photodiodes. In particular, the current I is indirectly generated when the radiological sensor uses a material layer called a scintillator that converts, beforehand, the x-rays into visible rays.

A voltage supply, originating from an external source, is delivered to a second input of the transimpedance amplifier 102, which is clocked by a clock Cl. The amplified signal $V_{out\_trans}$ is then transmitted to a first input of a comparator 103, which receives a threshold signal $V_{threshold}$ via a second input. The comparator 103 produces, as output, a signal $V_{out\_comp}$ that is representative of whether the threshold $V_{threshold}$ has been exceeded by the amplified signal $V_{out\_trans}$. The form of the signal output from the comparator 103 is then changed via an analog output stage 104.

FIG. 1b shows the variation in the signals input into and output from the comparator 103 and the signal output from the analog output stage 104. The various signals correspond to voltage signals expressed in volts.

Over one integrating period 100, the amplified signal $V_{out\_trans}$ is set to a reference voltage $V_{ref}$ during an initializing phase 110, then it is amplified during an integrating phase 120. The initializing phase 110 serves to set the input voltage of the transimpedance amplifier 102 to a reference voltage $V_{ref}$ that serves as a reference point for the integration of the current. This phase is necessary to stabilize the input reference voltage of the amplifier 102. The initializing phase 110 has a duration that is substantially shorter than the integrating phase 120. For example, the order of magnitude is an initializing phase 110 of duration three times shorter than the integrating phase 120.

When the amplified signal $V_{out\_trans}$ exceeds the threshold $V_{threshold}$, the output signal $V_{out\_comp}$ of the comparator 103 passes to a high value. The output signal detX of the detecting circuit thus passes to a high value once the amplified signal exceeds the detection threshold, in order to signal the detection of x-rays. The value of the detection threshold is programmable.

Figure 2:
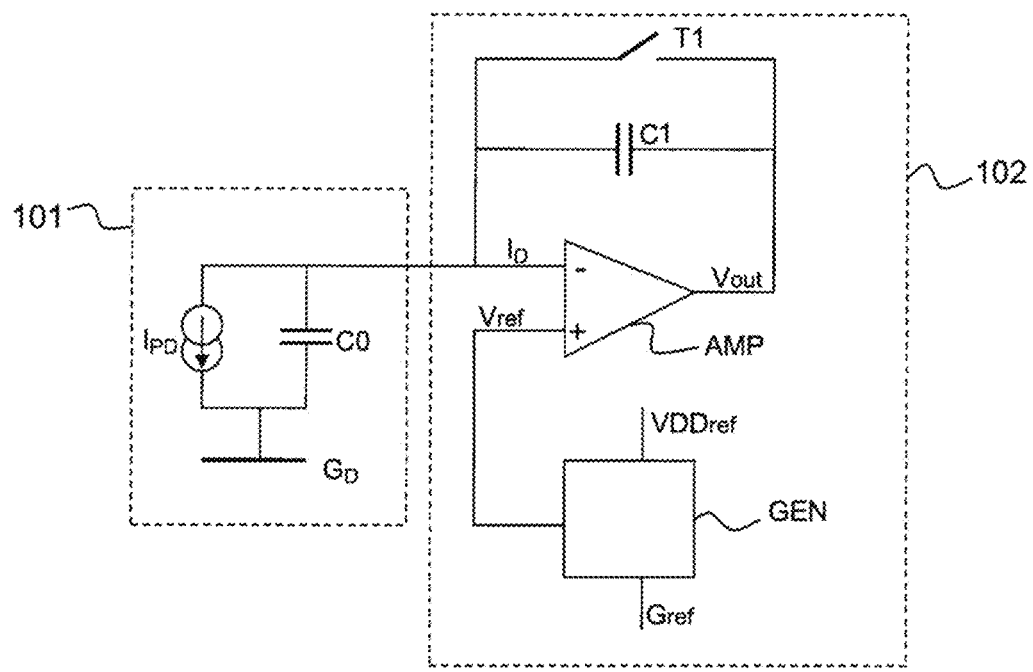
FIG. 2, a schematic of the architecture of an amplifying circuit according to the prior art.

FIG. 2 shows the architecture of a transimpedance amplifier 102 according to the prior art, connected to a set 101 of photodiodes that is modelled in the form of a current source $I_{PD}$ mounted in parallel with a parasitic capacitor C0 and connected to a ground $G_D$. The parasitic capacitor C0 models the sum of the parasitic capacitors of all the photodiodes.

The transimpedance amplifier 102 comprises an amplifier AMP, a generator GEN of a reference voltage $V_{ref}$, a capacitor $C_1$ and a switch T1.

The generator GEN produces a reference voltage $V_{ref}$ that is supplied to a first input (noninverting input +) of the amplifier AMP. The capacitor C1 is connected between the second input of the amplifier AMP and its output and allows the amplification gain of the signal to be adjusted. The switch $T_1$ is also connected between the second input of the amplifier AMP and its output. The generator GEN produces the reference voltage $V_{ref}$ from supplies external to the detecting circuit. The external supplies are represented in FIG. 2 in the form of a positive external supply $VDD_{ref}$ and a negative external supply $GND_{ref}$. The second input of the transimpedance amplifier (inverting input) is attacked by the current $I_D$ generated by the set 101 of photodiodes when the latter are activated by an x-ray flux.

During the initializing phase 110 (represented in the timing diagrams of FIG. 1b), the switch T1 is in closed position, this implying that the output voltage $V_{out}$ of the amplifier AMP is equal to the reference input voltage $V_{ref}$. During the integrating phase 120, the switch T1 is placed in its open position and the amplifier AMP then amplifies the input signal. Its transfer function is given by the following relationship, with A the gain of the amplifier AMP:

$$Vout = \frac{1}{-\frac{C1-C0}{A}+C1} \int I dt + Vref = \frac{1}{-\frac{C1-C0}{A}+C1} I_{PD} \times \Delta t + Vref \quad (1)$$

The gain of the transimpedance amplifier in particular depends on two parameters. It depends on the choice of the sampling frequency, which affects the integration time interval $\Delta t$, but also on the capacitance of the capacitor C1. The lower said capacitance is, the higher the amplification gain. Moreover, the variations $DV_{ref}$ in the input voltage $V_{ref}$ and the output voltage $V_{out}$ are also related by the relationship (2):

$$Vout = \left(1 + \frac{C0}{C1}\right) * DVref \quad (2)$$

The relationship (2) represents a parasitic transfer function that adds to the main transfer function of the amplifier, i.e. the transfer function given by relationship (1). The sum of the parasitic capacitors C0 has a capacitance significantly higher than the capacitor C1 that is integrated and the capacitance of which must be limited in order to preserve the amplification gain. Typically, the order of magnitude of the sum of the parasitic capacitors C0 is 100 pF whereas the order of magnitude of the capacitor C1 is 50 fF. Thus, the ratio C0/C1 is about 2000. The variations in the input voltage $V_{ref}$ are therefore amplified by a factor of 2000 to the output voltage $V_{out}$ of the amplifier AMP.

As indicated in the preamble, a problem exists when the reference voltage $V_{ref}$ is not stable, because variations in the amplitude of this voltage, even if they are small, induce variations in the output of the amplifier AMP that are amplified by a factor of 2000. Such variations may thus cause the threshold of the comparator 103 to be exceeded even in the absence of x-rays, i.e. when the current $I_D$ is zero. For example, a variation of 1 mV in the reference voltage during the integrating phase causes an increase of 2 V in the output of the amplifier AMP.

Now, the reference voltage $V_{ref}$ is produced by a generator GEN that is integrated into the detecting device, but that uses external supplies. Typically, these supplies are delivered by the personal computer or an equivalent device of the dentist, who connects the radiological sensor to this device via, for example, a USB link or any other suitable connecting means.

The fact of using external supplies potentially engenders variations and instability in the reference voltage $V_{ref}$ because of the random electromagnetic environment and of the instability inherent to the supplies delivered by a personal computer, which are not intended for a use dedicated to a high-precision sensor.

Furthermore, the problem also resides in the high capacitance of the parasitic capacitors C0 of the photodiodes because the set 101 of photodiodes is integrated into a matrix array of large size comprising a large number of photodiodes intended for medical imaging. These parasitic capacitors are inherent to the nature of the device and cannot be removed.

Moreover, it is also not possible to increase the capacitance of the capacitor C1 of the amplifier in order to compensate for the influence of the parasitic capacitors C0 because this would lead to a decrease in the amplification gain and therefore to the need to increase the intensity of the x-ray flux or to increase the integration time in order to obtain an output signal amplified to the same level. The increase of the exposure of the patient to x-rays runs contrary to the recommendations of medical standard-setting organizations and cannot therefore be a solution.

To correct this problem, the invention proposes to remove the parasitic transfer function given by relationship (2), which relates the reference voltage and the output voltage of the amplifier, in order to preserve only the amplification function given by relationship (1). To do this, the solution consists in generating a reference voltage $V_{ref}$ that is constant and that undergoes no variation, this effect being obtained by making this reference voltage independent of supplies external to the detecting circuit.

Figure 3:
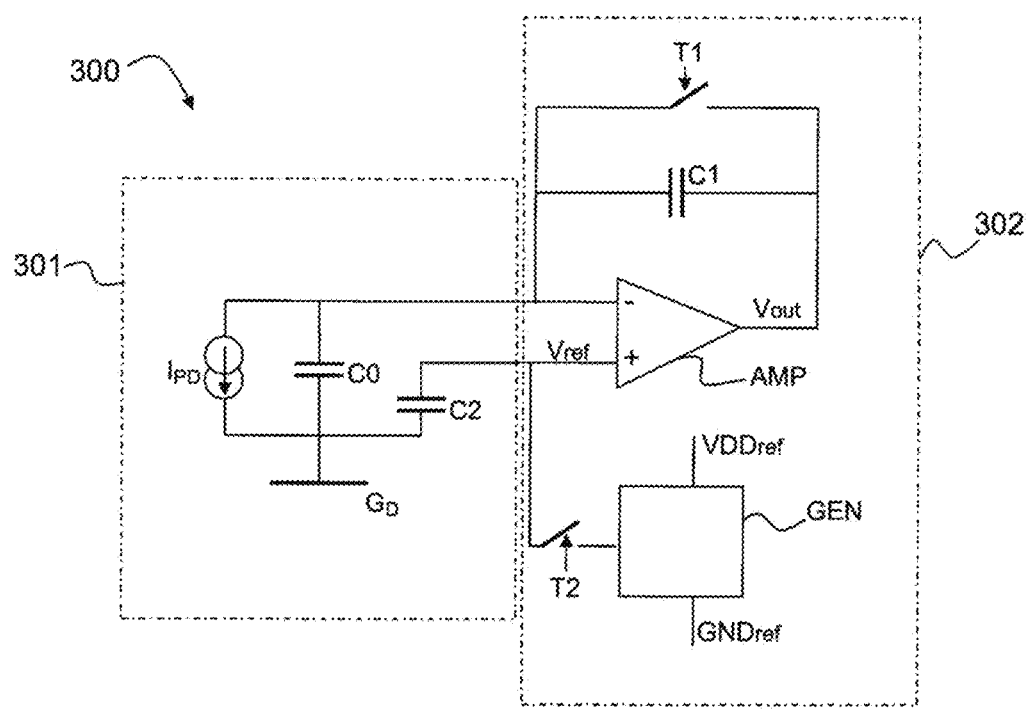
FIG. 3, a schematic of the architecture of a detecting circuit according to the invention.

FIG. 3 schematically shows the architecture of an x-ray detector 300 according to the invention. In this figure, only the set 301 of photodiodes and the amplifying circuit 302 are shown. The detector 103 and the analog output chain 104 illustrated in FIG. 1a are not modified and are therefore not shown.

The amplifying circuit 302 according to the invention includes the same elements as the amplifying circuit 102 according to the prior art illustrated in FIG. 2, the only difference being that a second switch $T_2$ is connected between the output of the generator GEN of the reference voltage $V_{ref}$ and the first input of the amplifier AMP.

The set 301 of photodiodes is also modified with respect to the set 101 of the circuit according to the prior art described in FIG. 2, by adding a storing capacitor C2 that is connected between the ground $G_D$ of the photodiodes and the first input of the amplifier AMP. This additional capacitor C2 may be obtained via a particular technique using some of the photodiodes, this technique being described in more detail further on in the description. As explained in more detail below, it is important for the additional capacitor C2 to be connected to the same ground $G_D$ as the photodiodes producing the current I on the second input of the amplifier AMP.

When the circuit is placed under voltage, the first switch $T_1$ and the second switch T2 are closed. During a first portion of the initializing phase, the reference voltage $V_{ref}$ is generated by the generator GEN and the capacitor C2, which is connected to the output of the generator GEN, is charged with the reference voltage $V_{ref}$.

During a second portion of the initializing phase, the second switch T2 is opened. The reference voltage $V_{ref}$ is stored by the capacitor C2 and supplies the first input of the amplifier AMP with a reference voltage that is stable and independent of the generator GEN. Specifically, opening the switch T2 allows the first input of the amplifier AMP to be isolated from the exterior environment of the circuit. The duration of the second portion of the initializing phase is necessary to guarantee a stability in the input reference voltage $V_{ref}$ of the amplifier AMP. When the second switch T2 is opened, the reference voltage $V_{ref}$ is then produced by the additional capacitor C2 and, during this action, a parasitic pulse may be generated. If the first switch T1 is opened simultaneously with the second switch T2, the parasitic pulse may propagate to the output of the amplifier and generate an undesired parasitic amplitude variation. For this reason, a delay is necessary between the opening of the second switch T2 and the opening of the first switch T1, this delay corresponding to the stabilization of the reference voltage $V_{ref}$ following the opening of the second switch T2. The duration of the second portion of the initializing phase must be minimized in order to prevent the integrating phase from being shortened.

The integrating phase is therefore then activated by opening the first switch T1 in order to activate the loop of the amplifier via the capacitor C1 and to amplify the current produced by the photodiodes. During the integrating phase, the second switch T2 is kept open.

The fact that the introduced additional capacitor C2 is connected to the same ground $G_D$ as the photodiodes also allows, during the integrating phase, stability to be increased because the two input channels of the amplifier AMP are referenced to the same ground and have the same leakage currents. For example, if the capacitor C2 were connected to a ground exterior to the circuit, potential variations in this ground could engender variations in the reference voltage stored on the capacitor. The fact of using the same ground for the photodiodes and for the additional capacitor C2 allows the influence of variations in the ground to be inhibited because, if they exist, they symmetrically impact both the current produced by the photodiodes and the reference voltage stored on the capacitor C2.

According to one particular embodiment of the invention, the additional capacitor C2 is produced by grouping a plurality of photodiodes, initially intended to be employed in the detection, with a view to masking them and using only their parasitic capacitor, their function of converting x-rays to current being inhibited. The term "mask" is employed to mean that a photodiode is made insensitive to x-rays using, for example, metal to cover the photodiode and to prevent the x-rays from reaching the photodiode. The masked photodiodes are thus connected to the voltage input of the amplifier AMP whereas unmasked photodiodes are connected to the current input of the amplifier AMP.

The choice of the number of photodiodes to be masked is a result of a compromise. The higher the number of photodiodes masked, the higher the capacitance of the capacitor C2 will be and the better able the latter will be to store the reference voltage over a duration corresponding to the integration duration. In contrast, a high number of masked photodiodes decreases by as many the number of photodiodes that may be used to detect x-rays. The number of detecting photodiodes directly influences the magnitude of the produced current, which must not be too low if a reliable detection is to be achieved.

It is however possible to mask some of the photodiodes dedicated to detection, in particular because, by producing the detecting circuit according to the invention, as illustrated in FIG. 3, untimely detections in the absence of current are prevented and it is thus possible to decrease the threshold value $V_{threshold}$ of detection, and therefore to adapt the circuit to an input current that is lower in magnitude due to a decreased number of detecting photodiodes.

Figure 4:
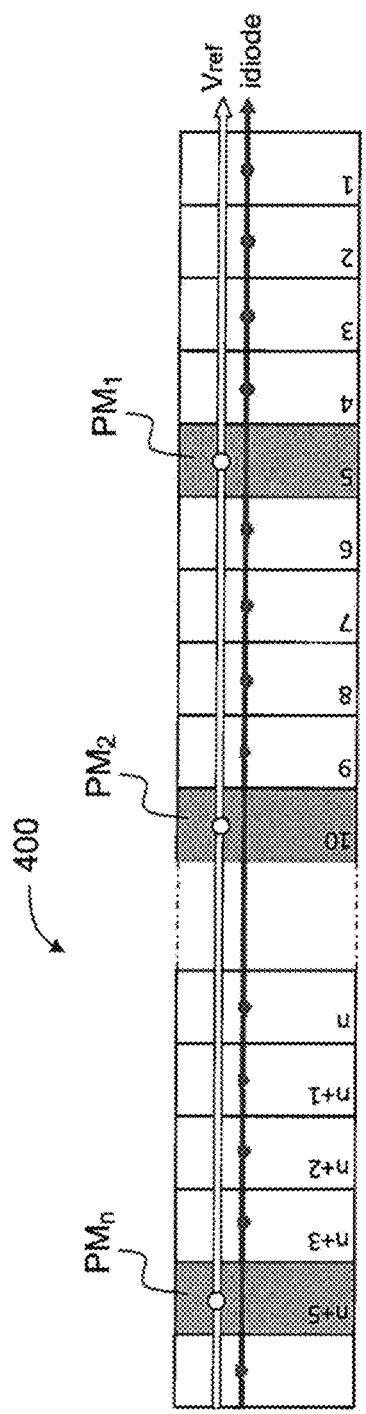
FIG. 4, a schematic of a strip of photodiodes of a detecting circuit according to one particular embodiment of the invention.

According to one particular embodiment illustrated in FIG. 4, the masked photodiodes are advantageously uniformly distributed within the set of photodiodes in order to take into account technological dispersions between the components and to achieve a better uniformity. Typically, a set of detecting photodiodes is arranged in a strip 400 that may be positioned in a row or a column of the matrix array of pixels of the radiological sensor. In this strip 400, the photodiodes are aligned and one photodiode in n is masked, with n being an integer higher than or equal to two. A good compromise consists, for example, in setting the value of n to 5. In FIG. 4, an example of distribution of masked photodiodes $PM_1$, $PM_2$, ..., $PM_n$ with a factor n equal to 5 has been shown.

The invention is however not limited to the particular arrangement illustrated in FIG. 4. In particular, the set 101 of photodiodes may be arranged in any other way, the chosen arrangement in particular depending on the design of the radiological sensor. The best operating mode of the invention corresponds, as indicated, to masked photodiodes positioned uniformly within the set of photodiodes, but the invention may also extend to nonuniformly positioned masked photodiodes, for example to masked photodiodes grouped at one end of a strip 400.

The invention claimed is:

1. A circuit for detecting the appearance of x-rays with a view to triggering a radiological image capture, comprising a set of photodiodes that is connected to a ground in parallel with a first capacitor, an amplifying circuit and a second capacitor, the amplifying circuit comprising an amplifier and a voltage source and being connected, via a first input, to the output of the set of photodiodes, the second capacitor being connected between the ground and a second input of the amplifier, and the amplifying circuit further comprising:

Means for charging the second capacitor with a reference voltage generated by the voltage source during a first portion of an initializing phase of the detecting circuit;

Means for isolating the second input of the amplifier from the voltage source during a second portion of the initializing phase of the detecting circuit; and A third capacitor connected between the first input of the amplifying circuit and the output of the amplifier in order to integrate the current generated by the set of photodiodes during a detecting phase following the second portion of the initializing phase.

2. The detecting circuit of claim 1, wherein the amplifying circuit further comprises a first switch connected between the first input and the output of the amplifier.

3. The detecting circuit as claimed in claim 1, wherein the amplifying circuit further comprises a second switch connected between the second input of the amplifier and the output of the voltage source.

4. The detecting circuit of claim 3, wherein the second switch is configured to be in closed position during the first portion of the initializing phase in order to charge the second capacitor with a reference voltage generated by the voltage source.

5. The detecting circuit of claim 4, wherein the second switch is configured to pass to open position during the second portion of the initializing phase in order to isolate the second input of the amplifier from the voltage source.

6. The detecting circuit as claimed in claim 4, wherein the first switch is configured to be in closed position during the initializing phase.

7. The detecting circuit as claimed in claim 2, wherein provision is made for means for opening the first switch after the end of the initializing phase.

8. The detecting circuit as claimed in claim 1, wherein the second capacitor is produced by masking some of the detecting photodiodes and by connecting the output of the masked photodiodes to the second input of the amplifier.

9. The detecting circuit of claim 8, wherein the masked photodiodes are uniformly distributed within the set of detecting photodiodes.

10. The detecting circuit of claim 9, wherein the proportion of masked photodiodes with respect to the detecting photodiodes is about 1/n with n an integer at least equal to two.

11. The detecting circuit as claimed in claim 1, furthermore comprising a comparator for comparing the output voltage of the amplifier to a threshold voltage.

12. The detecting circuit of claim 11, wherein said circuit is able to produce a signal for triggering image capture when the output voltage of the amplifier exceeds the threshold voltage.

13. A radiological image sensor comprising a circuit for detecting the appearance of x-rays with a view to triggering a radiological image capture as comprising a set of photodiodes that is connected to a ground in parallel with a first capacitor, an amplifying circuit and a second capacitor, the amplifying circuit comprising an amplifier and a voltage source and being connected, via a first input, to the output of the set of photodiodes, the second capacitor being connected between the ground and a second input of the amplifier, and the amplifying circuit further comprising:

Means for charging the second capacitor with a reference voltage generated by the voltage source during a first portion of an initializing phase of the detecting circuit;

Means for isolating the second input of the amplifier from the voltage source during a second portion of the initializing phase of the detecting circuit; and A third capacitor connected between the first input of the amplifying circuit and the output of the amplifier in order to integrate the current generated by the set of photodiodes during a detecting phase following the second portion of the initializing phase.

14. The detecting circuit of claim 13, wherein the second capacitor is produced by masking some of the detecting photodiodes and by connecting the output of the masked photodiodes to the second input of the amplifier.

15. The detecting circuit of claim 14, wherein the masked photodiodes are uniformly distributed within the set of detecting photodiodes.

16. The radiological image sensor of claim 13, wherein the amplifying circuit comprises a first switch connected between the first input and the output of the amplifier, a second switch connected between the second input of the amplifier and the output of the voltage source, wherein the second switch is configured to be in closed position during the first portion of the initializing phase in order to charge the second capacitor with a reference voltage generated by the voltage source and the first switch is configured to be in closed position during the initializing phase.

17. The radiological image sensor of claim 13, wherein the second capacitor is produced by masking some of the detecting photodiodes and by connecting the output of the masked photodiodes to the second input of the amplifier.

18. The radiological image sensor of claim 17, wherein the masked photodiodes are uniformly distributed within the set of detecting photodiodes.

19. The radiological image sensor of claim 18, wherein the proportion of masked photodiodes with respect to the detecting photodiodes is about 1/n with n an integer at least equal to two.

* * * * *